(12) United States Patent
Harada et al.

(10) Patent No.: US 9,108,997 B2
(45) Date of Patent: Aug. 18, 2015

(54) METHOD FOR RECYCLING ORGANIC RUTHENIUM COMPOUND FOR CHEMICAL VAPOR DEPOSITION

(71) Applicant: TANAKA KIKINZOKU KOGYO K.K., Tokyo (JP)

(72) Inventors: Ryosuke Harada, Ibaraki (JP); Shunichi Nabeya, Ibaraki (JP); Toshiyuki Shigetomi, Ibaraki (JP); Masayuki Saito, Ibaraki (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 14/396,861

(22) PCT Filed: Jun. 6, 2013

(86) PCT No.: PCT/JP2013/065682
§ 371 (c)(1),
(2) Date: Oct. 24, 2014

(87) PCT Pub. No.: WO2013/183703
PCT Pub. Date: Dec. 12, 2013

(65) Prior Publication Data
US 2015/0087851 A1    Mar. 26, 2015

(30) Foreign Application Priority Data
Jun. 7, 2012  (JP) ................. P2012-129428

(51) Int. Cl.
| | | |
|---|---|---|
| *C07F 17/02* | (2006.01) | |
| *C07F 15/00* | (2006.01) | |
| *B01J 23/44* | (2006.01) | |
| *C07C 45/79* | (2006.01) | |
| *C07C 45/85* | (2006.01) | |
| *B01J 23/42* | (2006.01) | |
| *B01J 23/46* | (2006.01) | |
| *B01J 25/02* | (2006.01) | |

(52) U.S. Cl.
CPC ............ *C07F 15/0046* (2013.01); *B01J 23/42* (2013.01); *B01J 23/44* (2013.01); *B01J 23/462* (2013.01); *B01J 25/02* (2013.01); *C07C 45/79* (2013.01); *C07C 45/85* (2013.01)

(58) Field of Classification Search
CPC .. C07F 15/0046; C07F 15/0053; C07C 49/92
USPC ............................................ 556/40, 41, 136
See application file for complete search history.

(56) References Cited

U.S. PATENT DOCUMENTS

| | | | |
|---|---|---|---|
| 6,884,463 | B2 | 4/2005 | Kitada et al. |
| 7,419,699 | B2 | 9/2008 | Kitada et al. |
| 2003/0045736 | A1 | 3/2003 | Saito |
| 2003/0180463 | A1 | 9/2003 | Saito |
| 2003/0203102 | A1 | 10/2003 | Saito et al. |
| 2011/0318488 | A1 | 12/2011 | Saito et al. |
| 2012/0282414 | A1 | 11/2012 | Saito et al. |

FOREIGN PATENT DOCUMENTS

| | | |
|---|---|---|
| JP | 2002-53961 A | 2/2002 |
| JP | 2003-104994 A | 4/2003 |
| JP | 2003-306472 A | 10/2003 |
| JP | 3507417 B2 | 3/2004 |
| JP | 4162366 B2 | 10/2008 |
| JP | 2009-46720 A | 3/2009 |
| JP | 4746141 B1 | 8/2011 |
| JP | 2012-6858 A | 1/2012 |
| WO | 2011/052453 A1 | 5/2011 |

*Primary Examiner* — Sudhakar Katakam
(74) *Attorney, Agent, or Firm* — Roberts & Roberts, LLP (57) ABSTRACT

The present invention is a method for recycling an organic ruthenium compound for chemical vapor deposition, wherein an unreacted organic ruthenium compound is extracted from a used raw material through a thin film formation process. The method includes the following steps (a) to (c). (a) A modification step in which the used raw material and a hydrogenation catalyst are brought into contact with each other in a hydrogen atmosphere, thereby hydrogenating an oxidized organic ruthenium compound in the used raw material. (b) An adsorption step in which the used raw material and an adsorbent are brought into contact with each other, thereby removing impurities in the used raw material. (c) A restoration step in which the used raw material is heated at a temperature that is not lower than −100° C. and not higher than −10° C. with respect to the decomposition temperature of the organic ruthenium compound for eight hours or more, thereby adjusting the ratio of the isomers of the organic ruthenium compound in the used raw material.

19 Claims, 4 Drawing Sheets

FIG. 1

Carish (M+ = 412)

IMPURITY α (M+ = 410)

IMPURITY β (M+ = 288)

METHOD FOR RECYCLING ORGANIC RUTHENIUM COMPOUND FOR CHEMICAL VAPOR DEPOSITION

CROSS REFERENCE TO RELATED APPLICATIONS

This application is a U.S. national phase entry of International Application No. PCT/JP2013/065682 filed Jun. 6, 2013 which claims priority from Japanese patent application JP2012-129428 filed Jun. 7, 2012.

TECHNICAL FIELD

The present invention relates to a method for recycling an organic ruthenium compound to be used as a raw material in a chemical vapor deposition method such as a CVD method and an ALD method. In detail, it relates to a method for allowing raw materials, which have been used for manufacturing a thin film and have been recovered, to be in a state in which they can be reused.

BACKGROUND ART

As thin film electrode materials of semiconductor devices such as DRAM and FERAM, ruthenium or a ruthenium compound is used. Examples of methods for manufacturing a thin film include chemical vapor deposition methods such as a CVD method (chemical vapor phase vapor deposition method) and an ALD method (an atomic layer vapor deposition method). As the raw material compound to be used for such chemical vapor deposition methods, many organic ruthenium compounds have been known conventionally.

A manufacturing cost of thin films using an organic ruthenium compound by a CVD method or the like is based on the use efficiency of the organic ruthenium compound raw material, besides costs for the organic ruthenium compound as the raw material. The use efficiency is a ratio of a compound amount consumed for film formation reaction to the raw material mass which has been introduced into the surface of a substrate, and the use efficiency of the organic ruthenium compound by, for example, the CVD method becomes low, for example, 10% or less in many cases. If problems of the low use efficiency are left unaddressed, a cost for manufacturing a ruthenium thin film, and, in turn, price increase of various devices are caused. In addition, resource exhaustion of ruthenium as noble metal may occur.

Herein, the present applicants have conventionally developed a recycling technique of an organic metal compound, which include extracting unreacted organic metal compounds from a used raw material and purifying them into a reusable state as a method for reducing a film formation cost and avoiding problems of resource exhaustion (e.g., refer to Patent Literature 1). This recycling technique including allowing a raw material gas after thin film formation to pass through, for example, a cold trap, recovering it by cooling and condensing thereof, and further distilling this recovered material under appropriate conditions so as to purify and extract an organic metal compound. According to this recycling technique, it is possible to reduce thin film manufacturing cost by avoiding waste of organic metal compounds.

Furthermore, the present applicants have also found that the organic metal compound recovered as mentioned above has problems of contamination of product by side reaction with respect to film formation reaction or coloring, and it is difficult to remove such problems by purification means such as distillation and that such material cannot be reused as a thin film raw material. Then, the present applicants have also developed a recycling method including purification means for making a recovered organic metal compound into a reusable state (e.g., refer to Patent Literature 2).

The above-mentioned technique for recycling an organic metal compound by the present applicant is applied to many organic ruthenium compounds which are used in development, and has results as to the efficient use thereof. According to the present inventors, however, it is demonstrated that some types of organic ruthenium compounds cannot be made into reusable state even if the above-mentioned conventional purification process is carried out.

In this point, as an organic ruthenium compound for thin film formation, conventionally, it has been required to have a low melting point and being liquid at ordinary temperatures, a high vapor pressure, and being able to be easily vaporized. This makes importance on handling property of the raw material or efficiency at a thin film manufacturing time. However, in recent years, in addition to such properties, compounds corresponding to various reaction atmosphere, and compounds which make more importance on properties of the manufactured thin film have been required, and an organic ruthenium compound in response to this have been developed (e.g., refer to Patent Literature 3). These relatively new organic ruthenium compounds have been made to have more complexity including specificity of ligands to be coordinated, asymmetric property of different ligand to be coordinated, and the like, as compared with conventional one. Thus, from the studies by the present inventors, conventional recycling techniques cannot completely correspond to such relatively new organic ruthenium compounds.

CITATION LIST

Patent Literature

Patent Literature 1: Japanese Patent No. 4162366
Patent Literature 2: Japanese Patent No. 3507417
Patent Literature 3: Japanese Patent No. 4746141

SUMMARY OF THE INVENTION

Technical Problem

Then, the present invention has an object to provide a method for recycling an organic ruthenium compound for chemical vapor deposition in which a range of compounds to be treated can be expanded, and which is also effective with respect to relatively new recent organic ruthenium compounds.

Solution to Problem

In order to solve the above-mentioned problems, the present inventors have keenly studied and examined properties of the used raw material of organic ruthenium compounds for chemical vapor deposition, which have been developed recently. This study process is descried taking dicarbonyl-bis (5-methyl-2,4-hexanedionato) ruthenium (II) represented by the following chemical formula which is an organic ruthenium compound described in Patent Literature 3 as an example.

[Chemical Formula 1]

The present inventors have studied the component and the structure of the recovered dicarbonyl-bis(5-methyl-2,4-hexanedionato) ruthenium (II) after film formation reaction, and have found the below-mentioned three phenomena which are disorders to be excluded for reuse.

First phenomenon is a structural change due to oxidization of ligand of an organic ruthenium compound. In the case of dicarbonyl-bis(5-methyl-2,4-hexanedionato)ruthenium (II), as mentioned below, a compound in which hydrogen at a ligand end is detached is generated. This compound is thought to be generated by a partial structural change due to an atmosphere at the time of production of a thin film.

[Chemical Formula 2]

Second phenomenon is that an organic ruthenium compound is completely changed into a compound having a different structure. In dicarbonyl-bis(5-methyl-2,4-hexanedionato)ruthenium (II), a compound which has been changed into an organic ruthenium compound having the following structure is observed. This change can be regarded as a complete degeneration by thermal decomposition or the like.

[Chemical Formula 3]

The specifically important one of the investigation results by the present inventors is the third disorder described below. As also described in Patent Literature 3, dicarbonyl-bis(5-methyl-2,4-hexanedionato)ruthenium (II) includes three types of isomers. The present inventors have found that the organic ruthenium compound after the thin film formation reaction has the existence ratio of isomers which is changed and is in a state in which the ratio is different from the existence ratio of the raw material before use.

[Chemical Formula 4]

Isomer A

Isomer B

Isomer C

All of the first to third disorders with respect to the reuse of the used raw material mentioned above are considered to give an influence on thin film production. In particular, the change of the ratio of isomers, which is found by the inventors of the present application, cannot be found from the outer appearances of the recovered used raw material or by simple analyses, but as also described in Patent Literature 3, the change of the ratio cannot be ignorable for compounds whose isomer ratio is important. The above-mentioned phenomena are considered to occur not only in dicarbonyl-bis(5-methyl-2,4-hexanedionato)ruthenium (II) taken as an example but also in organic ruthenium compounds having an isomer.

Herein, as measures with respect to each of the above-mentioned phenomena, first of all, there is no other means for removing a compound, which has completely a different structure, mentioned as a second phenomenon. On the other hand, for a partial structural change (detachment of hydrogen) of the organic ruthenium compound as the first phenomenon, it is considered that the changed compound has reversibility and the compound can be returned to an original compound by hydrogenation (reduction treatment). This is more useful measure in securing the yield of an organic ruthenium compound as compared with a simple removing method.

Then, for corresponding to the change of the ratio of the isomers, which is the third phenomenon, it is not clear whether or not the phenomenon has reversibility. Thus, the present inventors have carried out further study, resulting in finding that an organic ruthenium compound whose isomer ratio is changed can be adjusted by carrying out heat treatment at a predetermined temperature for relatively long time, and can be recovered to the isomer ratio of the original raw material before use. Then, the present inventors have found a method for allowing the used organic ruthenium compound to be completely reusable compound through combination with specific means with respect to the above-mentioned first and second phenomena, and have reached the present invention.

That is to say, the present invention relates to a method for recycling an organic ruthenium compound for chemical vapor deposition in which an unreacted organic ruthenium compound is extracted from a used raw material which has undergone a thin film formation process, and the method includes the following steps.

(a) A modification step in which the used raw material and a hydrogenation catalyst are brought into contact with each other in a hydrogen atmosphere, thereby hydrogenating an oxidized organic ruthenium compound in the used raw material.

(b) An adsorption step in which the used raw material and an adsorbent are brought into contact with each other, thereby removing impurities in the used raw material.

(c) A restoration step in which the used raw material is heated at a temperature that is not lower than $-100°$ C. and not higher than $-10°$ C. with respect to the decomposition temperature of the organic ruthenium compound for eight hours or more, thereby adjusting a ratio of isomers of the organic ruthenium compound in the used raw material.

Hereinafter, each step of the method for recycling an organic ruthenium compound in accordance with the present invention is described in detail.

A modification step in which the recovered used raw material is brought into contact with hydrogen and a hydrogenation catalyst is a step in which oxidized (detachment of hydrogen) organic ruthenium compound is reduced (hydrogenated), and is returned to an unreacted organic ruthenium compound. This step can allow an organic ruthenium compound which may affect a film formation process to disappear. Furthermore, since an original organic ruthenium compound is generated with this treatment, the yield of the organic ruthenium compound can be improved although slightly. Note here that the present invention is directed to treatment of an organic ruthenium compound including mixed isomers, but an organic ruthenium compound to be treated with this step may be derived from any isomers. For example, when organic ruthenium compounds in which hydrogen is equally detached in each isomer exist, all of them can be reacted, and they are expected to be returned to an organic ruthenium compound from which each of them is derived.

As the hydrogenation catalyst to be used in the modification step, any of a platinum catalyst, a palladium catalyst, a ruthenium catalyst, and a Raney nickel catalyst is preferably used. An amount of catalyst for hydrogenation is preferably $1/1000$ to the equal amount with respect to the weight of the used raw material. However, with the cost and efficiency in this step taken into account, the amount is particularly preferably $1/60$ to $1/40$ with respect to the weight of the used raw material. Note here that as the supported rate of a catalyst component (platinum, palladium, ruthenium, or the like) in each catalyst, a general range (5 to 10 mass %) can be applied. Furthermore, in this step, it is necessary to allow the used raw material to pass through a hydrogen gas. As the hydrogen, hydrogen with high purity is preferable.

The used raw material is brought into contact with an adsorbent in the adsorption step is to remove generated impurities when an organic ruthenium compound is completely changed in film formation. The impurities are required to be removed firstly because they affect the film formation reaction, and secondly because they do not have reversibility. Herein, examples of the adsorbent include activated carbon, silica gel, zeolite, alumina, and the like. A preferable example is activated carbon.

In this adsorption step, note here that in order to completely remove impurities generated as different substances from the used raw material, a sufficient reaction field is preferably provided. The amount of impurities is not constant, but the amount (ratio) of the impurities is relatively high, it is difficult to completely remove the impurities when the reaction field is small. Also the above-mentioned Patent Literature 3 describes use of activated carbon or the like for treatment of a recovered organic metal compound, but a main object of this conventional technique is decolorization, and the use amount of the activated carbon or the like is not limited. On the contrary, a main object of an adsorbent treatment in the present invention is not decolorization but removing of impurity. Therefore, an adsorbent whose specific surface area of 500 $m^2/g$ to 1500 $m^2/g$ is used, and the use amount is preferably $1/10$ to 10 times as the weight of the used raw material. The use amount of the adsorbent is more preferably $1/5$ to the equal amount of the weight of the used raw material although it depends upon the content of the impurities in the used raw material.

Note here that the order of the thus described modification step and adsorption step is not necessarily limited. This is because the steps improve the purity of the organic ruthenium compound from different effects, respectively.

Furthermore, both the modification step and the adsorption step can be carried out simultaneously. Since the catalyst to be used in the modification step supports the catalyst metal (for example, palladium and platinum) using activated carbon as a carrier, this carrier can act as an adsorbent. Therefore, when the use amount of the hydrogenation catalyst is set based on the amount of the activated carbon (carrier) which is necessary for the adsorption step, both the hydrogenation treatment and the adsorption treatment can be carried out simultaneously. In this case, however, when the amount of the activated carbon necessary for the adsorption step is large, it is necessary to use the hydrogenation catalyst in an amount that is more than necessary for the modification step, which may raise the treatment cost as a whole by the cost of the catalyst (more expensive than that of the activated carbon). Furthermore, in the modification step, hydrogen atmosphere with high purities is needed. When a large amount of catalysts are placed, it may catch fire. Therefore, the modification step and the adsorption step are carried out separately when the treatment cost and safety are taken into account.

Then, the most characteristic step in the method for recycling an organic ruthenium compound in accordance with the present invention is a restoration step of heating the used raw material so as to adjust an isomer ratio. The restoration step carries out heating at a temperature that is not lower than $-100°$ C. and not higher than $-10°$ C. on the basis of the decomposition temperature of the organic ruthenium compound. This is because temperatures of less than $-100°$ C. do not cause a change in the ratio of the isomers, and temperatures of more than $-10°$ C. may cause decomposition of the organic ruthenium compound. It is more preferable that the heating temperature is preferably not less than $-50°$ C. with respect to the decomposition temperature in order to improve the restoration efficiency.

Then, setting of the heating time is also necessary in the heat treatment in the restoration step. In this step, the adjustment of the isomer ratio can be completed with a relatively long time after heating. Specifically, heating for eight hours or more is required. Preferably, the heating time is 12 hours or more. It is not particularly necessary to set the upper limit of the heating time. However, when the heating temperature is optimized, fluctuation is reduced in the isomer ratio of the used raw material after 24 hours have passed. Therefore, when the working efficiency is taken into account, the heating time is preferably 48 hours or less.

Note here that a heating atmosphere for the restoration step includes inert gas atmospheres such as a nitrogen and an argon gas, and the heating is carried out while stirring is carried out. Furthermore, this restoration step may be carried out before the modification step and the adsorption step. However, since a slight amount of an organic ruthenium compound is generated by hydrogenation treatment in the modification step, it is preferable that the ratio of the isomers is adjusted after hydrogenation treatment.

The organic ruthenium compound in the used raw material which has undergone the above-described modification step, adsorption step, and restoration step does not include impurities which is difficult to be separated, and has a state whose isomer ratio is restored to the state before use. When the used raw material after use is subjected to distillation treatment, an organic ruthenium compound can be separated, thus enabling the material to be reused.

Specific examples of an organic ruthenium compound in which the method for recycling in accordance with the present invention is useful include the following compounds including dicarbonyl-bis(5-methyl-2,4-hexanedionato)ruthenium (II) represented by Chemical Formula 1.

[Chemical Formula 5]

(wherein the substituent R denotes a linear chain or branched chain alkyl group.)

[Chemical Formula 6]

(wherein the substituent R denotes a linear chain or branched chain alkyl group.)

[Chemical Formula 7]

(wherein the substituent R denotes a linear chain or branched chain alkyl group.)

Further specific examples of the organic ruthenium compound represented by the above-mentioned chemical formulae 5 to 7 include the following organic ruthenium compounds (the number of carbon atoms of the substituent R is 2 to 4).

TABLE 1

| Name | Structural Formula |
|---|---|
| dicarbonyl-bis (2, 4-hexanedionato)ruthenium (II) | |
| dicarbonyl-bis(5-methyl-2,4-hexane dionato)ruthenium (II) | |

TABLE 1-continued

| Name | Structural Formula |
|---|---|
| dicarbonyl-bis(2,4-heptanedionato)ruthenium (II) | |
| dicarbonyl-bis(5,5-dimethyl-2,4-hexanedionato)ruthenium (II) | |
| dicarbonyl-bis(5-methyl-2,4-hexanedionato)ruthenium (II) | |
| dicarbonyl-bis(6-methyl-2,4-heptanedionato)ruthenium (II) | |

TABLE 2

| Name | Structural Formula |
|---|---|
| bis(2,4-hexanedionato)(norbornadiene)ruthenium (II) | |
| bis(5-methyl-2,4-hexanedionato)(norbornadiene)ruthenium (II) | |

TABLE 2-continued

| Name | Structural Formula |
| --- | --- |
| bis(2,4-heptanedionato)(norbornadiene)ruthenium (II) | |
| bis(5,5-dimethyl-2,4-hexanedionato)(norbornadiene)ruthenium (II) | |
| bis(5-methyl-2,4-heptanedionato)(norbornadiene)ruthenium (II) | |
| bis(6-methyl-2,4-heptanedionato)(norbornadiene)ruthenium (II) | |

TABLE 3

| Name | Structural Formula |
| --- | --- |
| bis(2,4-hexanedionato)(cyclooctadiene)ruthenium (II) | |

TABLE 3-continued

| Name | Structural Formula |
| --- | --- |
| bis(5-methyl-2,4-hexanedionato)(cyclooctadiene)ruthenium (II) | |
| bis(2,4-heptanedionato)(cyclooctadiene)ruthenium (II) | |
| bis(5,5-dimethyl-2,4-hexanedionato)(cyclooctadiene)ruthenium (II) | |
| bis(5-methyl-2,4-heptanedionato)(cyclooctadiene)ruthenium (II) | |
| bis(6-methyl-2,4-heptanedionato)(cyclooctadiene)ruthenium (II) | |

Note here that the method for recycling an organic ruthenium compound in accordance with the present invention is useful for the above-mentioned used raw material including mixture of isomers, but the method can be applied for conventionally used organic ruthenium compounds. The present invention includes a modification step and an adsorption step in addition to the restoration step because these are useful for reproduction of an organic ruthenium compound which does not include isomers.

Advantageous Effects of Invention

As described above, a method for recycling an organic ruthenium compound in accordance with the present invention can recycle also an organic ruthenium compound, which includes a plurality of isomers and whose isomer ratio is changed after use, to be made into a reusable state by restoring the ratio of the isomers. Furthermore, the method can modify and remove an organic ruthenium compound whose partial or entire structure is changed due to the use of a hydrogenation catalyst and an adsorbent.

DESCRIPTION OF EMBODIMENTS

First Embodiment

In this embodiment, as an organic ruthenium compound for chemical vapor deposition, a ruthenium thin film was formed of dicarbonyl-bis(5-methyl-2,4-hexanedionato)ruthenium (II) represented by Chemical Formula 1 (hereinafter, referred to as "Carish" which is a trade name of this compound), and a used raw material in which a wasted gas was recovered by a cold trap. Then, this used raw material was subjected to a modification step, an adsorption step, and a restoration step, respectively, so as to examine the reusability.

Figure 1:
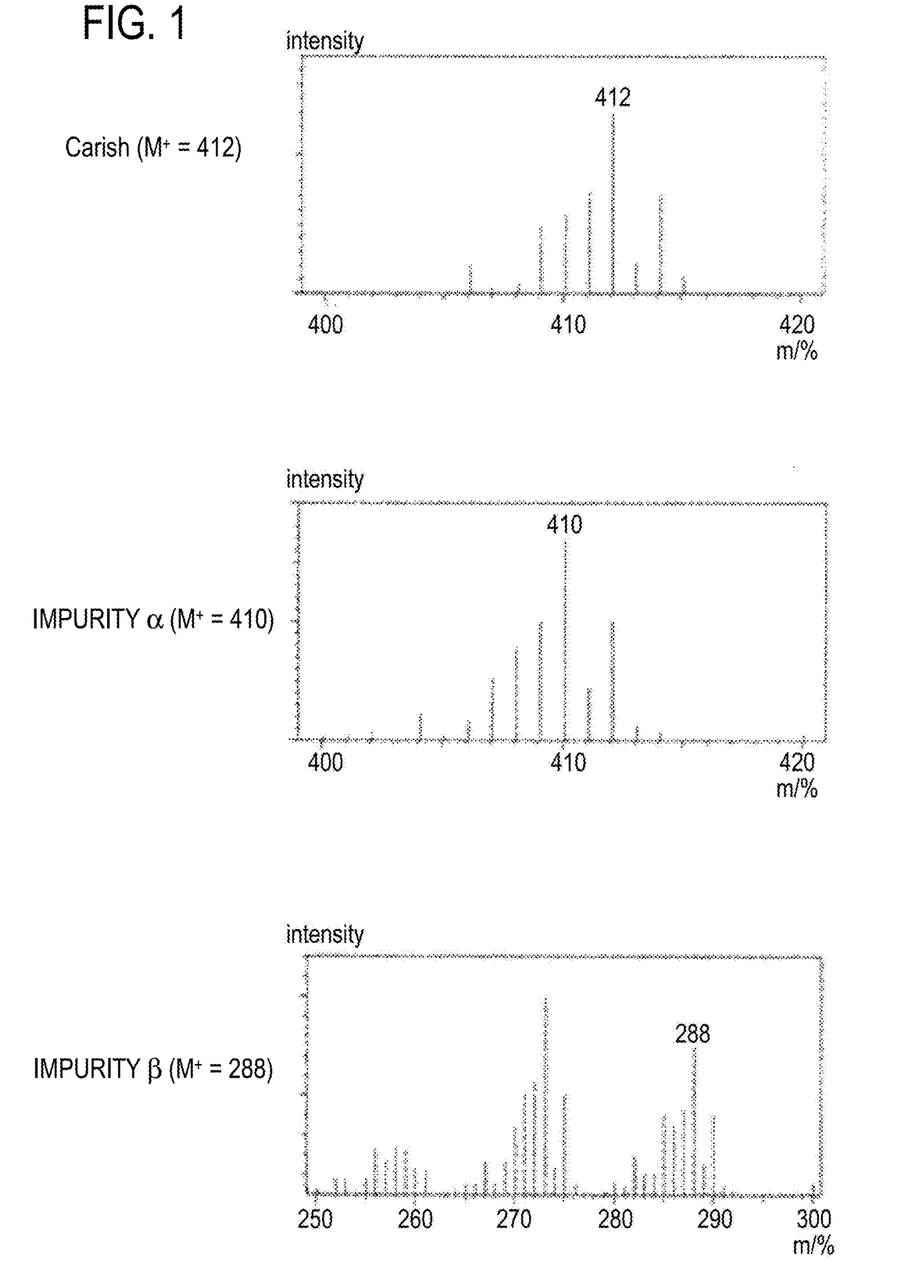
FIG. 1 illustrates GC-MS spectra of Carish, impurities α and β, which are observed in a used raw material.

Firstly, the property of the recovered used raw material was subjected to analysis search. In this analysis search, firstly, the used raw material was subjected to a qualitative analysis by gas chromatograph mass spectrometric analysis (GC-MS). In the analysis by the GC-MS, in the raw material before use, only mass spectrum derived from Carish (a region in the vicinity of $M^+=412$) was observed, but in the used raw material, in addition to this, two mass spectra were observed (a region in the vicinity of $M^+=410$ and a region in the vicinity of $M^+=288$) (FIG. 1). Among these two mass spectra, the former mass spectrum is thought to be derived from an organic ruthenium compound in which hydrogen atom at the Carish end is detached (compounds represented by the above-mentioned chemical formula 2: hereinafter, for convenience, referred to as impurity α) from the molecular weight value. It is estimated that the latter is a diene-arene complex of ruthenium generated by the decomposition of Carish (compound represented by the above-mentioned chemical formula 3: hereinafter, for convenience, referred to as impurity β). From this GC-MS analysis, it was demonstrated that the used raw material had two impurities generated by partial or entire change of the Carish.

Figure 2:
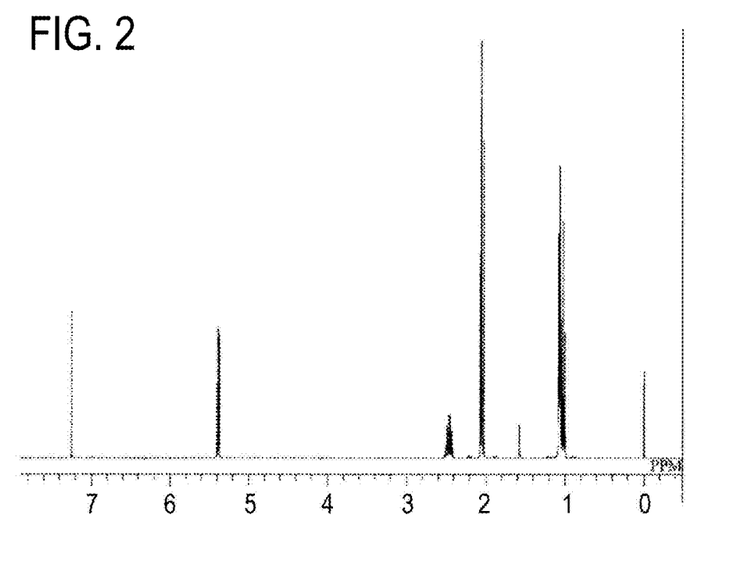
FIG. 2 is an overall view of $^1$H-NMR spectrum of the used raw material.
Figure 3:
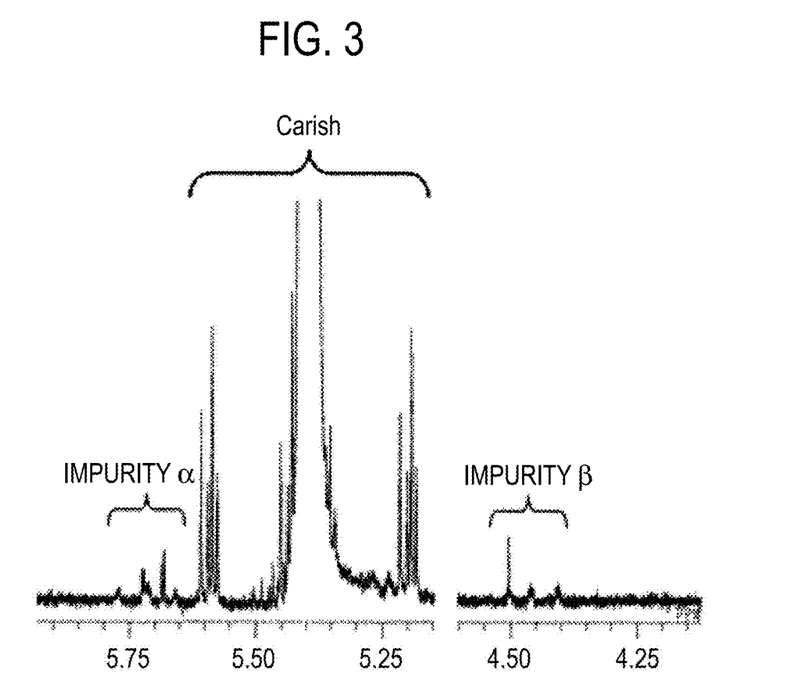
FIG. 3 is an enlarged view of $^1$H-NMR spectrum of the used raw material.

Next, the used raw material was subjected to NMR analysis ($^1$H-NMR measurement) to ensure the presence of impurity again and to ensure the isomer ratio of Carish in the used raw material. FIG. 2 shows a $^1$H-NMR spectrum of the used raw material, and FIG. 3 is an enlarged view thereof. In FIG. 3, it is estimated that a peak around 5.15 to 5.60 ppm in a chemical shift value (δ) of the $^1$H-NMR spectrum is a peak derived from Carish, a peak around 5.6 to 5.8 ppm in δ is a peak derived from the impurity α, and a peak around 4.4 to 4.6 ppm in δ is a peak derived from the impurity β. The isomer ratio of Carish in the used raw material can be estimated from this $^1$H-NMR spectrum. Herein, as to four peaks showing the presence of non-equivalent four protons observed around δ5.35 to δ5.45 ppm, one having a peak around δ5.42 ppm is referred to as an "isomer A," one having peaks around δ5.40 ppm and around δ5.38 ppm is referred to as an "isomer B," and one having a peak around δ5.39 ppm is referred to as an "isomer C". The designation of the isomers A to C follows the Chemical Formula 4. The ratio of isomers can be calculated from the area ratio of each peak. Note here that the identification of each isomer based on the $^1$H-NMR spectrum is described in detail in Patent Literature 3.

The ratios of the isomers of the impurity α of the raw material before use and the used raw material, which have been calculated based on the $^1$H-NMR spectrum, are as follows. As shown in Table 4, the ratio of the isomers of the used raw material was observed to be changed from the ratio of the isomers of the raw material before use.

TABLE 4

|  | Ratio of isomers (A:B:C) |
| --- | --- |
| Raw material before use | 16.7:53.0:30.3 |
| Used raw material | 17.6:54.9:27.5 |

The used raw material that had been subjected to the above-mentioned preliminary analysis examination was subjected to recycling processes in the following order.

[Modification Step]

To 100 g of the used raw material and 2 g of palladium catalyst (carbon carrier), 2 L of hexane was added, and this mixture was stirred at 50° C. and hydrogenation treatment was carried out by bubbling of hydrogen gas for two hours. After the reaction solution was filtered to remove palladium catalysts, hexane was removed by evaporation under reduced pressure by using a rotary evaporator. When GC-MS and $^1$H-NMR measurement of the used raw material after modification were carried out, the peak derived from the impurity α disappeared in both analyses. However, the peak of the impurity β survived remained.

[Adsorption Step]

Next, 100 g of the used raw material after the modification step was dissolved in 2 L of hexane. Then, adsorption treatment was carried out by allowing a solution of the used raw material in hexane to pass through a column filter loaded with 100 g of the activated carbon (trade name: SX-plus, specific surface area: 1100 $m^2$/g). Thereafter, hexane was removed by evaporation under reduced pressure by using a rotary evaporator. When GC-MS and $^1$H-NMR measurement of the used raw material after adsorption treatment were carried out, the peak derived from the impurity β disappeared in both analyses.

[Restoration Step]

The used raw material after the above-mentioned modification step and adsorption step was subjected to the restoration step by heat treatment. The used raw material (100 g) was heated in an argon gas atmosphere to 150° C. This treatment temperature takes the decomposition temperature of Carish, that is, 200° C., into consideration. Herein, $^1$H-NMR measurement of the used raw material was carried out after two hours, eight hours, and 24 hours had passed after the start of heat treatment, and the change of the ratio of the isomers according to the lapse of time. The measurement results are shown in FIG. 4.

Figure 4:
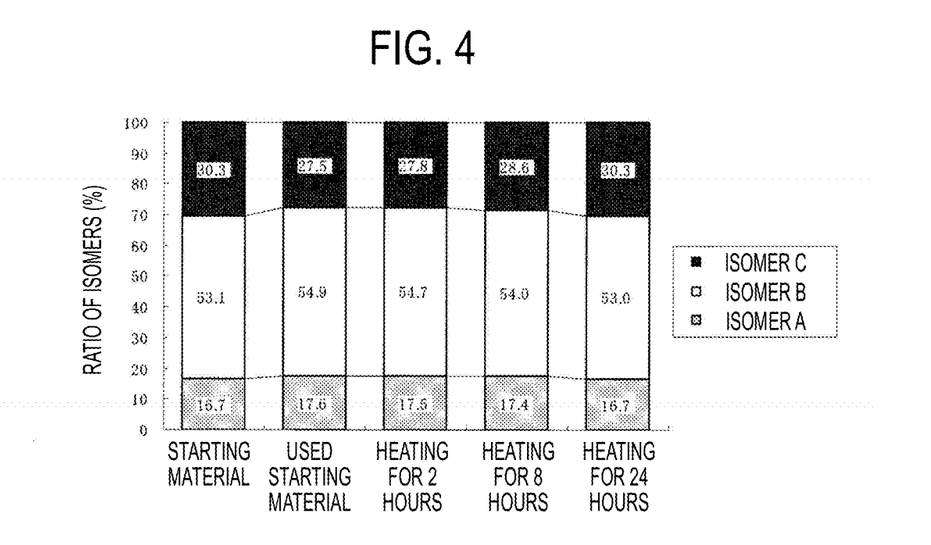
FIG. 4 is a graph showing the change of the ratio of isomers at each heating time in the restoration step in accordance with the first embodiment.

From FIG. 4, the change in the ratio of the isomers was hardly observed after heating for about two hours, the change occurred after about eight hours had passed, and restoration to the ratio of the isomers before use was completed after 24 hours of heating.

Next, the used raw material which had undergone the above-mentioned modification step, adsorption step, and restoration step was distilled to extract Carish and a ruthenium thin film was manufactured in order to observe the possibility of reuse thereof. The distillation of the used raw material was carried out in the conditions at a heating temperature of 160°

C. and pressure of 80 Pa. Then, the yield of the extracted Carish was 95% (the weight of the trap recovered used raw material was defined as a reference weight).

The film formation test of the ruthenium thin film was carried out by using a CVD device in the following conditions.

Raw material solution temperature: 140° C.
Substrate temperature: 230° C.
Reactor vessel field pressure: 5.0 torr
Carrier gas: argon (flow rate: 200 sccm)
Reaction gas: oxygen (flow rate: 50 sccm)

Figure 5:
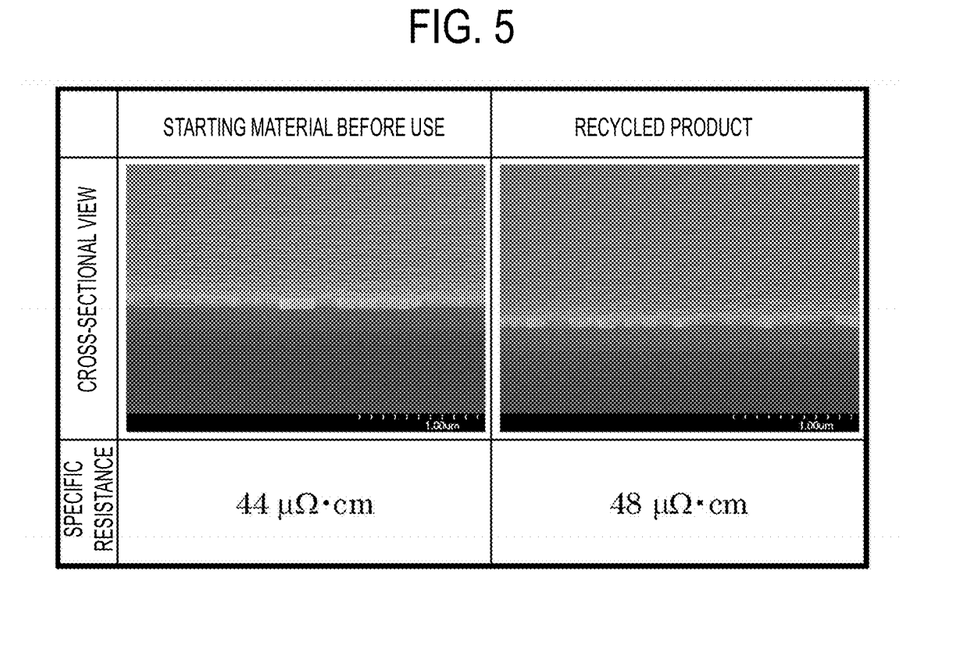
FIG. 5 illustrates a SEM photograph and specific resistance values of a ruthenium film formed with the use of a used raw material.

FIG. 5 shows photographs of a ruthenium film formed on a substrate. From FIG. 5, it is known that a ruthenium film of Carish after recycling can be a ruthenium film which is the equal level to Carish as the raw material before use. Furthermore, FIG. 5 also shows a specific resistance value measured in each ruthenium film. Also from the measurement result of the specific resistance, it can be observed that a ruthenium film that is equal level to the raw material before use can be formed. From the above mention, it is shown that an organic ruthenium compound of the used raw material after the modification step, adsorption step, and restoration step can be reused satisfactorily.

Second Embodiment

Next, a recycling process was carried out in which the process orders of the modification step and the adsorption step were interchanged. Under the same conditions as in the first embodiment, firstly, the adsorption step was carried out, and then the modification step was carried out. When GC-MS and $^1$H-NMR measurement of the used raw material after the treatment were carried out, the peaks derived from the impurities α and β disappeared. Thereafter, the used raw material was subjected to a recycling process through the restoration step as in the first embodiment. Then, when a ruthenium thin film was formed by using Carish extracted from the used raw material, a thin film having an excellent property was obtained.

Third Embodiment

Herein, the used raw material was treated by changing the types of activated carbons as the adsorbent in the adsorption step. Instead of the activated carbon in the first embodiment, two types of activated carbons (an activated carbon B (trade name: SX-1G, specific surface area: 1000 m$^2$/g) and an activated carbon C (trade name: SX-II, specific surface area: 900 m$^2$/g) were used. Adsorption treatment was carried out by allowing the used raw material after modification treatment to pass through a column loaded with 100 g of the activated carbon B and 200 g of the activated carbon C. GC-MS and $^1$H-NMR measurement of each used raw material after treatment were carried out, the peaks derived from the impurities α and β disappeared in each used raw material. Thereafter, the used raw material was subjected to a recycling process through the restoration step as in the first embodiment. Then, when a ruthenium thin film was formed by using Carish extracted from the used raw material, thin film having an excellent property was obtained.

Fourth Embodiment

Furthermore, the used raw material was treated by simultaneously carrying out the modification step and the adsorption step in which the use amount of the hydrogenation catalyst in the modification step is increased. The modification treatment (simultaneously, the adsorption treatment) was carried out under the same conditions as in the first embodiment except that the use amount of the palladium catalyst in the modification treatment was 100 g. When GC-MS and $^1$H-NMR measurement of the used raw material after this treatment were carried out, the peaks derived from the impurities α and β disappeared. Thereafter, the used raw material was subjected to a recycling process through the restoration step as in the first embodiment. Then, when a ruthenium thin film was formed by using Carish extracted from the used raw material, a thin film having an excellent property was obtained.

Fifth Embodiment

This embodiment carried out recycling of a used raw material to be treated including bis(5-methyl-2,4-hexanedionato)(norbornadiene)ruthenium (hereinafter, referred to as "Runish" as the trade name). The Runish has a decomposition temperature of 210° C., and includes the following three types of isomers which are mixed with each other.

[Chemical Formula 8]

The used raw material in the amount of 100 g, which had been recovered after a thin film was produced by using Runish, was prepared, 2 g of palladium catalyst and 2 L of hexane were added to the used raw material, the mixture was stirred at 50° C., and modification treatment was carried out by bubbling of hydrogen gas for two hours. After the reaction solution was filtered to remove the palladium catalyst, adsorption treatment was carried out by allowing the solution to pass through a column filter loaded with 100 g of the activated carbon (trade name: SX-plus, specific surface area: 1100 m²/g). Thereafter, hexane was removed by evaporation under reduced pressure by using a rotary evaporator.

Figure 6:
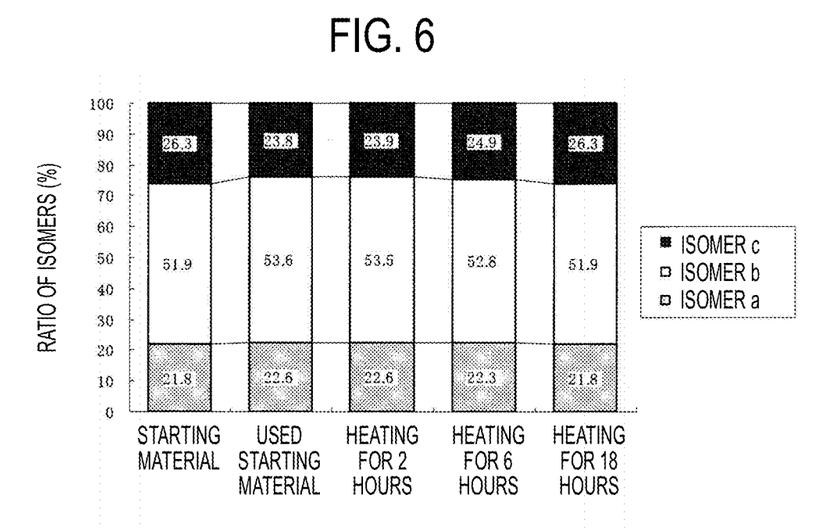
FIG. 6 is a graph showing the change of the ratio of isomers at each heating time in the restoration step in accordance with the fifth embodiment.

Next, the used raw material was heated in an argon gas atmosphere to 160° C. FIG. 6 shows the change of the ratio of the isomers depending upon the heating time. From FIG. 6, also in the used raw material including Runish as an organic ruthenium compound, restoration of the ratio of the isomers by heat treatment was observed. When GC-MS and $^1$H-NMR measurement of the used raw material after the restoration step were carried out, no peaks other than the peak of the Runish were observed.

Sixth Embodiment

In this embodiment, recycling of a used raw material to be treated including bis(5-methyl-2,4-hexanedionato)(cyclooctadiene)ruthenium was carried out. The bis(5-methyl-2,4-hexanedionato)(cyclooctadiene)ruthenium has a decomposition temperature of 210° C., and includes the following three types of isomers which are mixed with each other.

[Chemical Formula 9]

Isomer d

Isomer e

Isomer f

After a thin film was produced by using bis(5-methyl-2,4-hexanedionato) (cyclooctadiene)ruthenium, 100 g of the recovered used raw material was prepared, 2 g of palladium catalyst and 2 L of hexane were added to the used raw material, the mixture was stirred at 50° C., and modification treatment was carried out by bubbling of hydrogen gas for two hours. After the reaction solution was filtered to remove the palladium catalyst, adsorption treatment was carried out by allowing the solution to pass through a column filter loaded with 100 g of the activated carbon (trade name: SX-plus, specific surface area: 1100 m²/g). Thereafter, hexane was removed by evaporation under reduced pressure by using a rotary evaporator.

Figure 7:
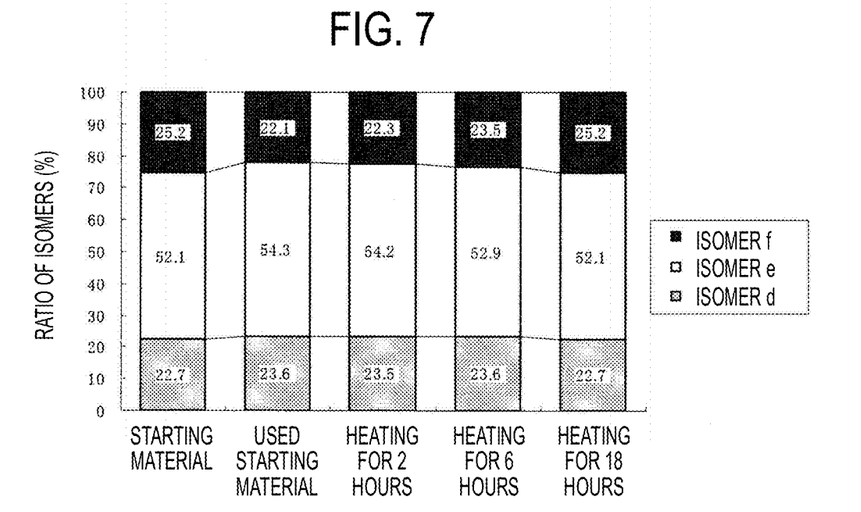
FIG. 7 is a graph showing the change of the ratio of isomers at each heating time in the restoration step in accordance with the sixth embodiment.

Next, the used raw material was heated in an argon gas atmosphere to 160° C. FIG. 7 shows the change of the ratio of the isomers depending upon the heating time. From FIG. 7, also in the used raw material including bis(5-methyl-2,4-hexanedionato)(cyclooctadiene)ruthenium as an organic ruthenium compound, restoration of the ratio of the isomers by heat treatment was observed. Also in this embodiment, when GC-MS and $^1$H-NMR measurement of the used raw material, which undergone the restoration step, were carried out, no peaks other than the peak of bis(5-methyl-2,4-hexanedionato)(cyclooctadiene)ruthenium were observed.

INDUSTRIAL APPLICABILITY

As described above, according to the present invention, an unreacted organic ruthenium compound in the used raw material through a chemical vapor deposition can be made into reusable state without wasting the material. The present invention can be applied to organic ruthenium compounds that have been developed recently. Therefore, according to the present invention, even when the use efficiency in the chemical vapor deposition process of an organic ruthenium compound is low, loss of the material does not occur. As a result, it is possible to reduce a cost for manufacturing a ruthenium thin film. Furthermore, by reusing an organic ruthenium compound that has been wasted conventionally, the present invention does not waste useful resources and therefore is useful in the problem of exhaustion of useful resources.

The invention claimed is:
1. A method for recycling an organic ruthenium compound for chemical vapor deposition by extracting an unreacted organic ruthenium compound from a used raw material which has undergone a thin film formation process, wherein the used raw material comprises any of the organic ruthenium compounds having the following chemical formulae, Chemical Formula 1, Chemical Formula 2, Chemical Formula 3, and the method comprising the following steps (a) to (c), wherein order of the steps (a) to (c) is arbitrary and the step (a) and the step (b) may be carried out simultaneously:
  (a) a modification step in which the used raw material and a hydrogenation catalyst are brought into contact with each other in a hydrogen atmosphere, thereby hydrogenating an oxidized organic ruthenium compound in the used raw material;
  (b) an adsorption step in which the used raw material and an adsorbent are brought into contact with each other, thereby removing impurities in the used raw material; and
  (c) a restoration step in which the used raw material is heated at a temperature that is not lower than −100° C. and not higher than −10° C. with respect to the decomposition temperature of the organic ruthenium compound for eight hours or more, thereby adjusting a ratio of isomers of the organic ruthenium compound in the used raw material;

wherein Chemical Formula 1 is wherein the substituent R is a linear chain or branched chain alkyl group;

Chemical Formula 2 is wherein the substituent R is a linear chain or branched chain alkyl group; and Chemical Formula 3 is wherein the substituent R is a linear chain or branched chain alkyl group.

2. The method for recycling an organic ruthenium compound according to claim 1, wherein the hydrogenation catalyst in the step (a) is any of a palladium catalyst, a platinum catalyst, a ruthenium catalyst, and a Raney nickel catalyst.

3. The method for recycling an organic ruthenium compound according to claim 1 wherein the adsorbent in the step (b) is any of an activated carbon, silica gel, zeolite, and alumina.

4. The method for recycling an organic ruthenium compound according to claim 1, wherein in a reaction condition of the adsorbent in the step (b), an adsorbent having a specific surface area of 500 $m^2/g$ to 1500 $m^2/g$, and a use amount of the adsorbent is 1/10 to 10 times as weight of the used raw material.

5. The method for recycling an organic ruthenium compound according to claim 1, wherein the organic ruthenium compound is extracted by distillation after processes by the steps (a) to (c).

6. The method for recycling an organic ruthenium compound according to claim 2, wherein the adsorbent in the step (b) is any of an activated carbon, silica gel, zeolite, and alumina.

7. The method for recycling an organic ruthenium compound according to claim 2, wherein in a reaction condition of the adsorbent in the step (b), an adsorbent having a specific surface area of 500 $m^2/g$ to 1500 $m^2/g$, and a use amount of the adsorbent is 1/10 to 10 times as weight of the used raw material.

8. The method for recycling an organic ruthenium compound according to claim 3, wherein in a reaction condition of the adsorbent in the step (b), an adsorbent having a specific surface area of 500 $m^2/g$ to 1500 $m^2/g$, and a use amount of the adsorbent is 1/10 to 10 times as weight of the used raw material.

9. The method for recycling an organic ruthenium compound according to claim 6, wherein in a reaction condition of the adsorbent in the step (b), an adsorbent having a specific surface area of 500 $m^2/g$ to 1500 $m^2/g$, and a use amount of the adsorbent is 1/10 to 10 times as weight of the used raw material.

10. The method for recycling an organic ruthenium compound according to claim 2, wherein the organic ruthenium compound is extracted by distillation after processes by the steps (a) to (c).

11. The method for recycling an organic ruthenium compound according to claim 3, wherein the organic ruthenium compound is extracted by distillation after processes by the steps (a) to (c).

12. The method for recycling an organic ruthenium compound according to claim 4, wherein the organic ruthenium compound is extracted by distillation after processes by the steps (a) to (c).

13. The method for recycling an organic ruthenium compound according to claim 6, wherein the organic ruthenium compound is extracted by distillation after processes by the steps (a) to (c).

14. The method for recycling an organic ruthenium compound according to claim 7, wherein the organic ruthenium compound is extracted by distillation after processes by the steps (a) to (c).

15. The method for recycling an organic ruthenium compound according to claim 8, wherein the organic ruthenium compound is extracted by distillation after processes by the steps (a) to (c).

16. The method for recycling an organic ruthenium compound according to claim 9, wherein the organic ruthenium compound is extracted by distillation after processes by the steps (a) to (c).

17. The method for recycling an organic ruthenium compound according to claim 1 wherein the organic ruthenium compound in the used raw material has Chemical Formula 1.

18. The method for recycling an organic ruthenium compound according to claim 1 wherein the organic ruthenium compound in the used raw material has Chemical Formula 2.

19. The method for recycling an organic ruthenium compound according to claim 1 wherein the organic ruthenium compound in the used raw material has Chemical Formula 3.

* * * * *